United States Patent
Kerman

(10) Patent No.: US 11,039,796 B2
(45) Date of Patent: Jun. 22, 2021

(54) HEART-RATE ADAPTIVE PULSE OXIMETRY

(71) Applicant: OWLET BABY CARE, INC., Lehi, UT (US)

(72) Inventor: Sean Kerman, Lehi, UT (US)

(73) Assignee: Owlet Baby Care, Inc., Lehi, UT (US)

(*) Notice: Subject to any disclaimer, the term of this patent is extended or adjusted under 35 U.S.C. 154(b) by 206 days.

(21) Appl. No.: 15/832,585

(22) Filed: Dec. 5, 2017

(65) Prior Publication Data

US 2018/0160986 A1 Jun. 14, 2018

Related U.S. Application Data

(60) Provisional application No. 62/433,524, filed on Dec. 13, 2016.

(51) Int. Cl.
*A61B 5/00* (2006.01)
*A61B 5/1455* (2006.01)
*A61B 5/024* (2006.01)

(52) U.S. Cl.
CPC ........ *A61B 5/7278* (2013.01); *A61B 5/02416* (2013.01); *A61B 5/14551* (2013.01); *A61B 5/725* (2013.01); *A61B 5/7257* (2013.01)

(58) Field of Classification Search
CPC ..... A61B 5/72; A61B 5/04028; A61B 5/7278; A61B 5/02416; A61B 5/14551; A61B 5/725; A61B 5/7257; A61B 5/02; A61B 5/02108; A61B 5/024; A61B 5/02405; A61B 5/02411; A61B 5/0255; A61B 5/02444; A61B 5/02438; A61B 5/02433; A61B 5/02427; A61B 5/025; A61B 5/02455; A61B 5/02422
USPC .................................................. 600/500–507
See application file for complete search history.

(56) References Cited

U.S. PATENT DOCUMENTS

| | | | |
|---|---|---|---|
| 2008/0167564 A1* | 7/2008 | Hete | A61B 5/0816 600/508 |
| 2014/0073960 A1* | 3/2014 | Rodriguez-Llorente | A61B 5/7246 600/479 |
| 2015/0032447 A1* | 1/2015 | Gunawan | G10L 25/84 704/233 |
| 2015/0105666 A1* | 4/2015 | Strachan | A61B 5/0245 600/473 |
| 2016/0051158 A1* | 2/2016 | Silva | A61B 5/02416 600/479 |

(Continued)

*Primary Examiner* — David J. McCrosky
*Assistant Examiner* — Chanel J Jhin
(74) *Attorney, Agent, or Firm* — Workman Nydegger

(57) ABSTRACT

Embodiments are directed to methods and systems for adaptive heart rate monitoring. In one scenario, a method for adaptive heart rate monitoring includes receiving, from a pulse-oximeter, a sensor signal, where the sensor signal is photoplethysmogram waveform. The method next includes generating a frequency-domain photoplethysmogram waveform by applying a transform algorithm to the sensor signal, and dividing the resulting frequency-domain photoplethysmogram waveform into discrete frequency regions. The method further includes identifying a fundamental heart rate harmonic within one of the discrete frequency regions by analyzing each discrete frequency region according to a specified analytic algorithm, and triggering a user interface to display a biometric measurement corresponding to the identification of the fundamental heart rate harmonic.

16 Claims, 1 Drawing Sheet

(56) References Cited

U.S. PATENT DOCUMENTS

2016/0262637 A1* 9/2016 Delia .................... A61B 5/7455
2016/0361021 A1* 12/2016 Salehizadeh ......... A61B 5/0245
2019/0133534 A1* 5/2019 Hu ..................... A61B 5/02416

* cited by examiner

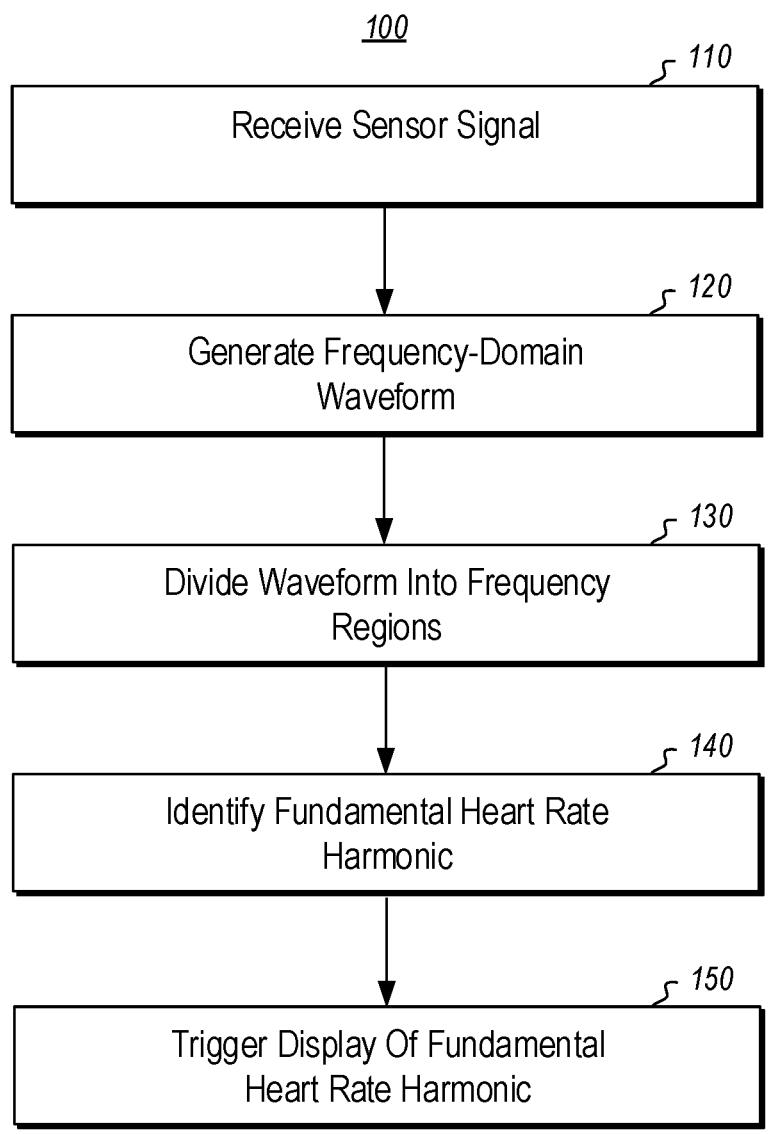

HEART-RATE ADAPTIVE PULSE OXIMETRY

CROSS-REFERENCE TO RELATED APPLICATIONS

This application is claims the benefit of and priority to U.S. Provisional Patent Application Ser. No. 62/433,524 filed on Dec. 13, 2016 and entitled "HEART-RATE ADAPTIVE PULSE OXIMETRY". This application expressly incorporates herein the entirety of the foregoing applications.

BACKGROUND

Electronic devices and systems have long been used to monitor physiological conditions in humans. Pulse-oximeters, for example, create photoplethysmograms (PPGs), by illuminating a patient's skin and measuring changes in light absorption as blood flows through the patient's veins. Fast Fourier Transforms (FFTs) are often used for determining heart rate from a photoplethysmogram or other physiological wave form. Various methods have been used to try to separate the fundamental heart rate frequency in the FFT from artifacts and from other harmonics. These methods, however, are inefficient and inflexible.

BRIEF SUMMARY

Embodiments described herein are directed to methods and systems for adaptive heart rate monitoring. In one embodiment, a method for adaptive heart rate monitoring includes receiving, from a pulse-oximeter, a sensor signal, where the sensor signal is photoplethysmogram waveform. The method next includes generating a frequency-domain photoplethysmogram waveform by applying a transform algorithm to the sensor signal, and dividing the resulting frequency-domain photoplethysmogram waveform into discrete frequency regions. The method further includes identifying a fundamental heart rate harmonic within one of the discrete frequency regions by analyzing each discrete frequency region according to a specified analytic algorithm, and triggering a user interface to display a biometric measurement corresponding to the identification of the fundamental heart rate harmonic.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which:

FIG. 1 illustrates a flowchart of an example method for adaptive heart rate monitoring.

DETAILED DESCRIPTION

As noted above, embodiments described herein are directed to methods and systems for adaptive heart rate monitoring. In one scenario, a method for adaptive heart rate monitoring includes receiving, from a pulse-oximeter, a sensor signal, where the sensor signal is photoplethysmogram waveform. The method next includes generating a frequency-domain photoplethysmogram waveform by applying a transform algorithm to the sensor signal, and dividing the resulting frequency-domain photoplethysmogram (PPG) waveform into discrete frequency regions. The method further includes identifying a fundamental heart rate harmonic within one of the discrete frequency regions by analyzing each discrete frequency region according to a specified analytic algorithm, and triggering a user interface to display a biometric measurement corresponding to the identification of the fundamental heart rate harmonic.

As used herein, the term "adaptive heart rate monitoring" generally refers to making changes to the way a heart rate is monitored, based on the heart rate itself. In some embodiments herein, the heart rate of a patient or other user is initially determined by performing a Fast Fourier Transform (FFT) on the PPG output of a pulse-oximeter. The FFT is performed to determine the fundamental heart rate harmonic, which is the best indication of the patient's actual heart beat. The heart rate monitoring may then be adapted to a specific patient according to their heart rate. This may be performed by breaking up the determined heart rate into N different heart rate ranges, and then using different criteria to evaluate heart rates in the different ranges. This allows more accurate and reliable selection of the fundamental heart rate harmonic.

For example, an adaptive heart rate monitoring system may compute an FFT of a PPG waveform, and the resulting N FFT bins may be broken up into M regions. The bins in each M region are assigned different criteria to determine if the bin should be considered as a candidate for the fundamental heart rate harmonic. These criteria or classification methods may be different for different heart rate ranges of an FFT-based heart rate measurement algorithm. For instance, heart rates over 200 beats per minute (BPM) are not common in neonates and, as such, the criteria or classification methods might specify that a heart rate above 200 BPM is only to be selected if there are no peaks below 200 BPM. Alternatively, signals below 60 BPM are typically artifact signals, and heart rates below 60 rarely occur if oxygen levels are >90% SpO2, where SpO2 represents a measure of oxygen saturation in a patient's blood. Thus, in such cases, heart rates below 60 BPM may only be selected if oxygen is <90% SpO2. Many such criteria may be used to distinguish between the fundamental heart rate harmonic and other artifact signals, harmonics or noise. These concepts will be explained further below with regard to method 100 of FIG. 1.

In view of the systems and architectures described above, methodologies that may be implemented in accordance with the disclosed subject matter will be better appreciated with reference to the flow chart of FIG. 1. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 1 illustrates a flowchart of a method 100 for adaptive heart rate monitoring. Method 100 includes receiving from a pulse-oximeter sensor a sensor signal, wherein the sensor signal comprises a photoplethysmogram waveform (110). The pulse-oximeter sensor may be attached to a patient in a variety of different locations, but most often, it is attached to the patient's finger. The pulse-oximeter emanates light which is shined into the patient's finger. Some of this light is reflected back to an optic sensor on the pulse-oximeter. The amount of light reflected back will vary based on the amount of blood in the patient's finger. Thus, as the patient's heart beats, blood flows to and from their finger, and this rhythmic blood flow causes periodic variations in the amount of reflected light, thereby allowing a heartbeat to be detected.

Although a pulse-oximeter is described herein as an example of a physiologic monitoring system, it will be understood that substantially any type of physiologic monitoring system may be used herein. Still further, while photoplethysmograms are used as an example of physiologic sensor signals, many different types of sensor signals may be used with the systems and methods described herein.

Method 100 next includes generating a frequency-domain photoplethysmogram waveform by applying a transform algorithm to the sensor signal (120). As noted above, one type of transform algorithm for generating a frequency-domain signal from a time-domain signal is a Fast Fourier Transform. FFTs may be applied to the photoplethysmogram signal to create a frequency-domain version of that signal. This resulting frequency-domain photoplethysmogram waveform is then divided into discrete frequency regions (130). The regions may include, for example, lower than 60 beats per minute, 60-120 BPM, 120-200 BPM, or higher than 200 BPM. Each of these regions may be analyzed separately using different criteria. For instance, the criteria may include an oxygen saturation level (SpO2) below or above which a heart rate would not be selected for identifying the fundamental heart rate harmonic. It will be understood that the BPM ranges identified above were chosen arbitrarily, and that other ranges may be used.

Method 100 further includes identifying a fundamental heart rate harmonic within one of the discrete frequency regions by analyzing each discrete frequency region according to a specified analytic algorithm (140). The specified analytic algorithm may include the criteria such as current oxygen saturation of the patient's blood. Each frequency region may thus be analyzed using a separate analytic algorithm that is appropriate to that frequency range. The frequency regions are analyzed to determine a fundamental heart rate harmonic. Once this has been identified, the method 100 triggers a user interface to display a biometric measurement corresponding to the identification of the fundamental heart rate harmonic (150). The user interface may be displayed on a more specialized electronic device such as a heart rate monitor, or may be displayed on a laptop, PC, smart phone, wearable device or other type of electronic device. The user interface displays the fundamental heart rate harmonic, as identified in at least one of the discrete frequency regions using the analytic algorithm specific to that region.

In cases where the physiologic monitoring signal is a photoplethysmogram, the photoplethysmogram signal may be fed into an FFT component, which may be comprised of hardware and/or software. The FFT component generates a frequency-domain photoplethysmogram waveform, which is then divided into discrete frequency regions according to criteria that may be specific to a patient or to a patient showing certain symptoms. In some cases, the FFT component may include a band pass filter which is used to divide the frequency-domain photoplethysmogram waveform into discrete frequency regions. The band pass filter can be designed to allow certain ranges of frequencies to pass through the filter, while blocking others. Thus, specified frequency bandwidths created by the band pass filter may form the discrete frequency regions.

Each of these discrete frequency regions may represent a different heart rate range. These ranges may be chosen arbitrarily, or may be preselected. Moreover, these ranges may be dynamically changed if desired by a user such as a doctor or nurse. Different selection criteria are used to evaluate heart rates in the different heart rate ranges. These selection criteria are based on physiological indicators such as oxygen saturation. For instance, a heart rate of 60 won't be selected for determining the fundamental heart rate harmonic unless the oxygen saturation reading is below a specified value.

Once a heart rate range has been identified, an FFT may be performed to determine the fundamental heart rate harmonic. Fourier transform bins resulting from the Fourier transform are divided into a specified number of regions. Bins in each region are assigned different specified criteria which are used to decide if the bin is to be considered as a candidate that represents the fundamental heart rate harmonic. Secondary information received from the patient, doctor, nurse, parent or other user may also be applied when determining which region or which bin to use. The secondary information may, for example, include age information for the patient. The secondary information may be applied as an input when dividing the resulting frequency-domain photoplethysmogram waveform into discrete frequency regions.

Accordingly, methods and systems are provided for adaptive heart rate monitoring. These methods and systems may be used with a variety of different physiologic monitoring systems and devices.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

I claim:

1. A method for adaptive heart rate monitoring and for subsequently modifying how a heart rate is monitored based on an initial result obtained from the adaptive heart rate monitoring, said method comprising:

receiving from a pulse-oximeter sensor a sensor signal that corresponds to a heart rate of a patient, wherein the sensor signal comprises a photoplethysmogram waveform;

generating a set of frequency bins by applying a transform algorithm to the sensor signal;

dividing the set of frequency bins into a plurality of discrete frequency regions, wherein:

a first subset of frequency bins selected from the set of frequency bins is associated with a first region, the first region further associated with a first region-specific criteria to determine if any of the first subset of frequency bins within the first region is a candidate for a fundamental heart rate harmonic of the patient, the first region-specific criteria being associated with a heart rate above two-hundred beats per minute, and a second subset of frequency bins selected from the set of frequency bins is associated with a different, second region, the second region further associated with a second region-specific criteria to determine if any of the second subset of frequency bins within the second region is a candidate for the fundamental heart rate harmonic of the patient, the second region-specific criteria being associated with a heart rate below sixty beats per minute and a measured oxygen level below ninety percent;

identifying the fundamental heart rate harmonic within the first subset of frequency bins or the second subset of frequency bins, based on evaluating the first subset of frequency bins in view of the first region-specific criteria, and based on evaluating the second subset of frequency bins in view of the second region-specific criteria;

triggering a user interface to display a biometric measurement corresponding to the fundamental heart rate harmonic; and in response to identifying the fundamental heart rate harmonic, modifying how the heart rate of the patient is subsequently monitored based on the heart rate itself, such that subsequent monitoring of the heart rate is adapted to the patient according to the patient's heart rate.

2. The method of claim 1, wherein the set of frequency bins is divided into the plurality of discrete frequency regions using a band pass filter.

3. The method of claim 1, wherein the plurality of discrete frequency regions represent different heart rate ranges.

4. The method of claim 3, wherein the first and second region-specific criteria are used to evaluate heart rates in the different heart rate ranges.

5. The method of claim 1, wherein the first and second region-specific criteria are based on physiological indicators.

6. The method of claim 1, wherein the transform algorithm comprises a Fourier transform algorithm.

7. The method of claim 6, wherein one or more Fourier transform bins resulting from the Fourier transform are divided into the plurality of discrete frequency regions.

8. The method of claim 1, wherein secondary information is received and applied as an input when dividing the set of frequency bins into the plurality of discrete frequency regions.

9. A computer system for adaptive heart rate monitoring, comprising:

one or more processors; and one or more computer-readable media having stored thereon executable instructions that, when executed by the one or more processors, configure the computer system to perform at least the following:

receive from a pulse-oximeter sensor a sensor signal that corresponds to a heart rate of a patient, wherein the sensor signal comprises a photoplethysmogram waveform;

generate a set of frequency bins by applying a transform algorithm to the sensor signal;

divide the set of frequency bins into a plurality of discrete frequency regions, wherein:

a first subset of frequency bins selected from the set of frequency bins is associated with a first region, the first region further associated with a first region-specific criteria to determine if any of the first subset of frequency bins within the first region is a candidate for a fundamental heart rate harmonic of the patient, the first region-specific criteria being associated with a heart rate above two-hundred beats per minute, and a second subset of frequency bins selected from the set of frequency bins is associated with a different, second region, the second region further associated with a second region-specific criteria to determine if any of the second subset of frequency bins within the second region is a candidate for the fundamental heart rate harmonic of the patient, the second region-specific criteria being associated with a heart rate below sixty beats per minute and a measured oxygen level below ninety percent;

identify the fundamental heart rate harmonic within the first subset of frequency bins or the second subset of frequency bins, based on evaluating the first subset of frequency bins in view of the first region-specific criteria, and based on evaluating the second subset of frequency bins in view of the second region-specific criteria;

trigger a user interface to display a biometric measurement corresponding to the fundamental heart rate harmonic; and in response to identifying the fundamental heart rate harmonic, modify how the heart rate of the patient is subsequently monitored based on the heart rate itself such that subsequent monitoring of the heart rate is adapted to the patient according to the patient's heart rate.

10. The computer system of claim 9, wherein the set of frequency bins is divided into the plurality of discrete frequency regions using a band pass filter.

11. The computer system of claim 9, wherein the plurality of discrete frequency regions represent different heart rate ranges.

12. The computer system of claim 11, wherein the first and second region-specific criteria are used to evaluate heart rates in the different heart rate ranges.

13. The computer system of claim 9, wherein the first and second region-specific criteria are based on physiological indicators.

14. The computer system of claim 9, wherein the transform algorithm comprises a Fourier transform algorithm.

15. The computer system of claim 14, wherein one or more Fourier transform bins resulting from the Fourier transform are divided into the plurality of discrete frequency regions.

16. The computer system of claim 9, wherein secondary information is received and applied as an input when dividing the set of frequency bins into the plurality of discrete frequency regions.

* * * * *